(12) United States Patent
McGovern (10) Patent No.: US 10,850,137 B2
(45) Date of Patent: Dec. 1, 2020

(54) METHOD OF RESHAPING A BODY PART

(71) Applicant: Meghan K. McGovern, Savannah, GA (US)

(72) Inventor: Meghan K. McGovern, Savannah, GA (US)

( * ) Notice: Subject to any disclaimer, the term of this patent is extended or adjusted under 35 U.S.C. 154(b) by 81 days.

(21) Appl. No.: 15/142,546

(22) Filed: Apr. 29, 2016

(65) Prior Publication Data

US 2017/0312068 A1 Nov. 2, 2017

(51) Int. Cl.
*A61Q 19/00* (2006.01)
*A61M 5/315* (2006.01)
*A61M 5/32* (2006.01)
*A61K 8/73* (2006.01)
*A61L 27/20* (2006.01)
*A61K 8/85* (2006.01)
*A61Q 19/08* (2006.01)
*A61L 27/52* (2006.01)
*A61B 17/00* (2006.01)

(52) U.S. Cl.
CPC .............. *A61Q 19/00* (2013.01); *A61K 8/735* (2013.01); *A61K 8/85* (2013.01); *A61L 27/20* (2013.01); *A61L 27/52* (2013.01); *A61M 5/31511* (2013.01); *A61M 5/3286* (2013.01); *A61Q 19/08* (2013.01); *A61B 2017/00792* (2013.01); *A61K 2800/91* (2013.01); *A61L 2400/06* (2013.01); *A61M 2210/0606* (2013.01)

(58) Field of Classification Search
CPC ....... A61F 2/0059; A61K 8/042; A61K 8/735; A61M 2210/0606; A61Q 19/00; A61Q 19/08
See application file for complete search history.

(56) References Cited

U.S. PATENT DOCUMENTS

| 4,497,075 A | 2/1985 | Niwa et al. |
| 5,236,456 A | 8/1993 | O'Leary et al. |
| 5,591,232 A | 1/1997 | Rahimi et al. |

(Continued)

OTHER PUBLICATIONS

Sharad, Jaishree, Dermal Fillers for the Treatment of Tear Trough Deformity: A Review of Anatomy, Treatment Techniques, and their Outcomes, Oct.-Dec. 2012, Journal of Cutaneous and Aesthetic Surgery, 5(4), 229-238.*

(Continued)

*Primary Examiner* — Bhisma Mehta
*Assistant Examiner* — Hong-Van N Trinh
(74) *Attorney, Agent, or Firm* — Jason P. Webb; Pearson Butler (57) ABSTRACT

A method of reshaping a body part including the step of injecting a quantity of filler material into a subperiosteal plane of a facial region thereby depositing a body of filler between the periosteum and bone of the facial region. The method includes the step of piercing a periosteum of the facial region with a syringe. The method includes the step of drawing backwards a plunger of the syringe to ascertain whether a tip of a needle of the syringe is within a blood vessel. The filler may include a hyaluronic acid gel. The method of reshaping a body part includes the step of applying pressure to the body of filler to adjust a shape of the body of filler. The step of injecting is repeated in the following order of priority: first the temporal line of fusion, second the zygoma, third the malar, and fourth the jaw line.

17 Claims, 6 Drawing Sheets

(56) References Cited

U.S. PATENT DOCUMENTS

| | | | |
|---|---|---|---|
| 5,942,499 | A | 8/1999 | Radomsky |
| 8,038,665 | B2 | 10/2011 | Burgess |
| 8,142,817 | B2 | 3/2012 | Giampapa |
| 8,377,013 | B2 | 2/2013 | Biyani |
| 8,480,681 | B2 | 7/2013 | Jordan |
| 8,603,184 | B2 | 12/2013 | Rizzoli et al. |
| 8,613,938 | B2 | 12/2013 | Akella et al. |
| 8,641,696 | B2 | 2/2014 | Barbour |
| 8,815,228 | B2 | 8/2014 | Boutros |
| 2009/0069739 | A1 | 3/2009 | Mohamed |
| 2009/0209456 | A1* | 8/2009 | Sweis ............... A61K 8/49 |
| | | | 514/1.1 |
| 2012/0039862 | A1 | 2/2012 | Borodic |
| 2013/0150307 | A1* | 6/2013 | Turkel ............ A61K 38/164 |
| | | | 514/17.6 |

OTHER PUBLICATIONS

Salti, Giovanni and Rauso, Raffaele, Facial Rejuvenation with Fillers: The Dual Plane Technique, Jul.-Sep. 2015, Journal of Cutaneous and Aesthetic Surgery, 8(3), 127-133.*

Nanda, Soni and Bansal, Shikha, Upper face rejuvenation using botulinum toxin and hyaluronic acid fillers, 2013, Indian Journal of of Dermatology, Venereology and Leprology, 79(1), 32-40.*

Luthra, Amit, Shaping Lips with Fillers, Jul.-Sep. 2015, Journal of Cutaneous and Aesthetic Surgery, 8(3), 139-142.*

Buckingham, Edward D. et al., Volume Rejuvenation of the Facial Upper Third, Facial Plastic Surgery, vol. 31, No. 1 (Year: 2015).*

Midwest Facial Plastic Surgery & Aesthetic SkinCare, Full Face Correction with Radiesse Volumizing Filler featuring Dr. Joseph Campanelli, Jun. 12, 2012, Youtube, https://www.youtube.com/watch?v=Gw5qC09xem8&t=186s.*

* cited by examiner

METHOD OF RESHAPING A BODY PART

BACKGROUND OF THE INVENTION

Field of the Invention

The present invention relates to surgical procedures, specifically to a method of reshaping a body part, particularly including the face.

Description of the Related Art

A facelift, technically known as a rhytidectomy (from Ancient Greek rhytis "wrinkle"+ektome "excision", surgical removal of wrinkles), is a type of cosmetic surgery procedure used to give a more youthful facial appearance. There are multiple surgical and non-surgical techniques. Such usually involves the removal of excess facial skin, with or without the tightening of underlying tissues, and the re-draping of the skin on the patient's face and neck, fat transfers, and/or injecting material into the skin to change muscle operation (e.g. Botox), fill dermal volume (injected into the mid to deep dermis) and/or to stimulate new collagen production within the skin (which creates volume effects). Facelifts are effectively combined with eyelid surgery (blepharoplasty) and other facial procedures and are typically performed under general anesthesia or deep twilight sleep.

Human faces change over time and as we age. In general, children and young adults have very boxy, rectangular, vertical foreheads. As we enter our thirties, the forehead becomes less vertical (generally shifting backwards and losing mass to become less rectangular and more like a triangle). The forehead also generally flattens on the outer edges. Over time, the lining of the forehead bone fuses to the bone at the temporal line of fusion (TLF). All of the lining of all of the bones is connected, so as the underlying support loses volume, the structures lose their scaffolding and shift downward. The outer aspect of the eye drifts down; the cheeks drift down; etc. The places in our face that are tethered to deeper structures cannot drift down as effectively, so the tissues crash into them. Then we get nasojugal folds (tear troughs), nasolabial folds, marionette lines, and jowls. Various techniques have been developed to try and fill soft tissue to counteract such changes.

Some improvements have been made in the field. Examples of references related to the present invention are described below in their own words, and the supporting teachings of each reference are incorporated by reference herein:

U.S. Pat. No. 5,236,456, issued to O'Leary et al., discloses an osteogenic composition is obtained from demineralized bone tissue.

U.S. Pat. No. 5,942,499, issued to Radomsky, discloses a bone growth-promoting composition is provided comprising hyaluronic acid and a growth factor. The composition has a viscosity and biodegradability sufficient to persist at the site of desired bone growth for a period of time sufficient to promote the bone growth. Preferably hyaluronic acid is used in a composition range of 0.1-4% by weight and preferred growth factor is bFGF, present in a concentration range of about $10^{-6}$ to 100 mg/ml.

U.S. Pat. No. 8,815,228, issued to Boutros, discloses a composition comprising an alloplastic injectable suspension for use as a dermal filler comprising a biocompatible and pliable material and a physiologically acceptable suspending agent is provided. A method of making a composition comprising an alloplastic injectable suspension for use as a dermal filler comprising a biocompatible and pliable material and a physiologically acceptable suspending agent, said method comprising admixing a biocompatible and pliable material with a physiologically acceptable suspending agent, is also provided. A method of augmenting soft tissue to provide long-term reduction of a skin defect, said method comprising stimulating collagen beneath the skin defect is further provided. In an embodiment of the method of augmenting soft tissue, the stimulation of collagen production is effected by injecting into the deep reticular dermis an a dermal filler, said dermal filler being an alloplastic injectable suspension and comprising a biocompatible and pliable material and a physiologically acceptable suspending agent.

U.S. Patent Application Publication No.: 2009/0069739, by Mohamed, discloses non-surgical methods and systems of facial restoration, and more particularly a multi-technique method utilizing tissue tightening, collagen shortening and remodeling with long term fillers to provide for non-surgical facial sculpting and lift are provided. The methods and systems address the predictable pattern of multi-layered volume loss of tissue from the skin to the bone as a result of aging.

The inventions heretofore known suffer from a number of disadvantages which include being difficult to perform, being expensive, being unsafe, being ineffective, being inefficient, being more damaging to the body, being difficult to perform, failing to reduce facial disharmony (resulting in an "unnatural" look), being slow to perform, causing too much bruising, and allowing filler to be absorbed quickly.

What is needed is a method of reshaping a body part that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available methods. Accordingly, the present invention has been developed to provide a safe and efficient method of reshaping a body part.

According to one embodiment of the invention, there is a method of reshaping a body part. The method may include the step of injecting a quantity of filler material into a subperiosteal plane of the body part thereby depositing a body of filler between a periosteum and bone of the body part. The method may include the step of piercing a periosteum of the body part with a syringe. The method of reshaping a body part may include the step of drawings backwards a plunger of the syringe to ascertain whether a tip of a needle of the syringe is within a blood vessel. The filler may include a hyaluronic acid gel. The method may include the step of applying pressure to the body of filler to adjust a shape of the body of filler.

According to one embodiment of the invention, there is a method of reshaping a face. The method may include the step of injecting a quantity of filler material into a subperiosteal plane of a facial region thereby depositing a body of filler between the periosteum and bone of the facial region. The method may include the step of piercing a periosteum of the facial region with a syringe. The method of reshaping a face may include the step of drawings backwards a plunger of the syringe to ascertain whether a tip of a needle of the syringe is within a blood vessel. The filler may include a hyaluronic acid gel.

The method of reshaping a face may include the step of applying pressure to the body of filler to adjust a shape of the body of filler. A facial region may be selected from the group of facial regions consisting of: the temporal line of fusion, the zygoma, the malar, and the jaw line. The step of injecting may be repeated in the following order of priority: first the temporal line of fusion, second the zygoma, third the malar, and fourth the jaw line.

According to one embodiment of the invention, there is a method of reshaping a face. The method may include the step of injecting a quantity of filler material into a subperiosteal plane of a facial region thereby depositing a body of filler between the periosteum and bone of the facial region. The method may further include the step of piercing a periosteum of the facial region with a syringe. The method of reshaping a face may include the step of drawing backwards a plunger of the syringe to ascertain whether a tip of a needle of the syringe is within a blood vessel. The filler may include a hyaluronic acid gel.

The method of reshaping a face may include the step of applying pressure to the body of filler to adjust a shape of the body of filler. A facial region may be selected from the group of facial regions consisting of: the temporal line of fusion, the zygoma, the malar, and the jaw line. The step of injecting may be repeated in the following order of priority: first the temporal line of fusion, second the zygoma, third the malar, and fourth the jaw line. The method may include the step of injecting a quantity of filler material subdermally to a facial region not having a bone backing.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which.

DETAILED DESCRIPTION OF THE INVENTION

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps.

"Comprising" is to be interpreted as including the more restrictive terms "consisting of" and "consisting essentially of."

Figure 1:
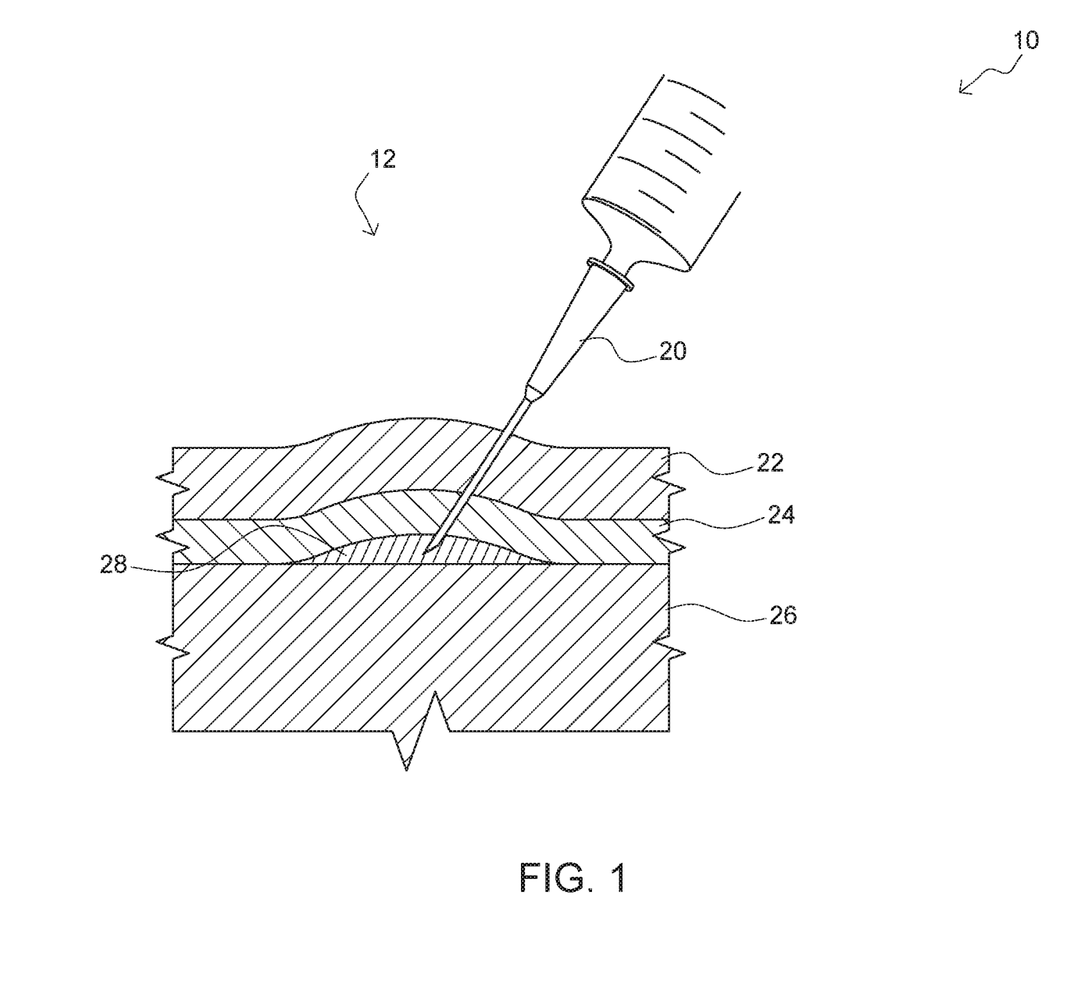
FIG. 1 is a partial side elevational cross-sectional view of body part having an injection step of a method of reshaping a body part carried out thereon, according to one embodiment of the invention.

FIG. 1 is a partial side elevational cross-sectional view of body part having an injection step of a method of reshaping a body part carried out thereon, according to one embodiment of the invention. There is shown a method of reshaping a body part 10, specifically the step of injecting a quantity of filler material into a subperiosteal plane of a body part 12. The illustrated subperiosteal plane is a region between the periosteum 24 and the bone 26 of the body part. A body part 12 will most often be a face/skull of a human, as such is a common place to desire to reshape, but it may include other body parts such as but not limited to any body part having a subperiosteal plane, such as but not limited to knees, hands, elbows, spines, fingers, collarbones, shoulders, ribs, and the like wherein reshaping may be desired. Further, the method may be carried out on animals that have similar subperiosteal regions as well.

In operation of the method, an operator will generally take a syringe (or other similar structure/method/device) filled with a filler material, choose a location where the filler material is to be deposited, pierce the skin with a needle of the syringe, continue to apply pressure towards the bone of the recipient until the needle pierces the periosteum and strikes the bone.

The bone, being very resistant to such piercing pressure, provides a "backstop" for the needle and also produces a different "feel" for the operator with regard to interaction with the needle tip (i.e. the periosteum is smoother and able to be pierced while bone is generally more rough and not able to be pierced). The operator confirms the placement of the tip of the needle as being in a region without blood vessels by creating negative pressure within the syringe chamber, generally by drawing back on the plunger. If the tip of the needle is placed improperly within a blood vessel then blood will enter up through the needle channel and into the chamber with the filler. In such a case, the needle would be repositioned and tested again.

Where no blood comes up into the chamber and the needle is "backstopped" directly by bone (thereby being through the periosteum) the operator then pushes filler from the chamber through the needle channel and into the subperiosteal plane at the tip of the needle in a desired amount. To be clear, the filler is not being injected into the skin, but instead beyond the skin into the space between the bone covering (periosteum) and the bone itself. The filler then causes a lifting effect on the flexible membranes above the bone (since the bone will not move). This lifting effect also reduces the effecting planar dimensions of the membranes (e.g. skin) thereby tightening the membranes and pulling against adjacent sections of the membranes. This advantageously reduces folds/wrinkles and lifts skin portions. Further, the reshaping of the region where the filler is placed can also advantageously create a more natural, normal, and/or more youthful appearance at the filler location. Such benefits will generally apply wherein bone mass has been lost due to factors such as but not limited to age, disease, malformation, injury and the like and combinations thereof.

The needle may then be withdrawn and the body of filler in the subperiosteal plane may be shaped (See FIG. 2, generally by application of pressure, e.g. from the operators thumb or some other blunt member/structure) to a desired shape. In particular, the injected body of filler will generally lift more than a desired amount in a region smaller than desired. Accordingly, applying pressure against the body of filler with the bone as a backstop may cause the body of filler to redistribute in wider area with less lifting effect. Accordingly, fewer injections are required to produce lifting over a larger area of the body part. As regions of the body part are so treated, desired reshaping occurs.

The illustrated method of reshaping a body part 10 includes the step of injecting a quantity of filler material 28 into a subperiosteal plane of the body part thereby depositing the filler 28 between a periosteum 24 and a bone 26 of a body part. The injection step may utilize a syringe to deposit the filler material in the desired location(s) or may use some other method, device or structure to accomplish the same, such as but not limited to a permanent port to the subperiosteal plane or a surgical method whereby cuts are made to allow for access to place filler within the subperiosteal plane.

The illustrated method 10 shows that a syringe 20, filled with a filler material 28, is inserted through the skin 22, piercing the periosteum 24. The syringe thereby injects the filler material 28 between the periosteum 24 and the bone 26 of a body part when the plunger is depressed by the operator thereof. The syringe may then be withdrawn to be used later to place filler in a different location.

The method of reshaping a body part 10 also includes the step of drawing backwards on a plunger of the syringe (or otherwise generating negative pressure and/or a vacuum) to ascertain whether a tip of a needle of the syringe is within a blood vessel or not, as it is undesirable to place filler within a blood vessel.

According to one embodiment of the invention, there is a method of reshaping a face including the step of injecting filler material in a subperiosteal plane near a temporal line of fusion. The periosteum is very stiff and the syringe may push through it. Once the tip of the syringe scrapes on the bone, the operator then draws back on the plunger of the syringe to be sure that the syringe is not in a blood vessel.

The operator selects locations where filler is to be injected. Generally, the operator first asks the recipient to clench and unclench their jaw (or grits teeth or shews gum, etc.) in order to tighten and loosen the muscles along the temporal line of fusion. This allows the operator to see/feel the path of the temporal line of fusion on the skull and thereby plot/plan the path of injections.

The operator may then inject filler into the subperiosteal plane just under the eyebrow and then upwards/backwards along the skull, still in the subperiosteal plane, following the temporal line of fusion (See FIG. 3, typically following the superior temporal line where there is no muscle and just to the inside of the inferior line where there is muscle if there is a concavity in that region) up/back into the scalp as appropriate. An advantage to following the temporal line of fusion is that the temporal line of fusion naturally protrudes a small amount from the surrounding area and injecting filler in such a location merely extends that same protrusion. Thus the regions that are filled have a natural look that blends in well with the natural contours of the head.

Standard syringes that come with the filler material kits may be used. A non-limiting example of such include Juvederm Voluma brand filler kits by Allergan, Inc., which filler comprises a modified form of hyaluronic acid (modified to include a high degree of cross-linking), a substance naturally present in skin. Other brands of fillers include but are not limited to: Perlane by Galderma S.A. Societe Anonyme of Switzerland, Juvederm UP of Allergan Inc., Artefill of Suneva Medical, Inc., Sculptra (poly-i-lactic acid) of Valeant International (Barbados) SRL Society of Barbados, and Radiesse of Merz North America, Inc. A recommended amount (generally 0.1 CC) of filler material may be used with each injection and then the operator will mold the filler into the proper shape by manual manipulation with fingers and/or thumb so that the filler material tapers into the native bone and looks natural (e.g. not like little horns). This results in 3D restoration/reshaping of frontal bone.

The operator may start at the hairline (which may reduce bruising), but in doing so it is possible that the client may not get proper reshaping of eyebrows and forehead. Accordingly, where reshaping of the eyebrows and/or forehead is desired, one would start at the eyebrows and/or forehead. Further, it is possible to inject into more medial portions of the forehead, but those tend to have less of an effect on the face itself and therefore are generally a less efficient utilization of the filler.

After injecting in the eyebrows/forehead/scalp, the operator may start injecting the mid-face, still in the subperiosteal plane. Starting at the zygoma (cheekbone), then proceeding to injections in the malar region (e.g. anterior cheeks, between zygoma and nose), then proceeding to the jaw line (typically at the frown tether point and the corner of the jaw), the operator is able to continue reshaping key regions of the face that have a high impact on the resultant shape, produce a natural look, and reduce wrinkles/folds efficiently.

It is generally better to start at the top of the face/head and not start at the jaw. It is believe that this is at least partially because the method lifts regions upwardly and therefore it is less effective to put material at the bottom that drag down until the method has properly lifted the top. For areas like the lip without bone backing, the doctor may finish with typical sub-dermal processes (e.g. mid to deep dermis fillers, muscle relaxers, collagen stimulators).

According to one embodiment of the invention, there is a technique for forehead filler and restoration. The technique includes locating the temporal line of fusion (TLF) by making a patient 'pretend to chew gum' thereby being able to find an edge of muscle insertion at lateral forehead. This may vary by 2-3 cm on each patient, and may be different on each side. Starting at the lateral eyebrow, place an injection needle at upper orbital rim on forehead side of TLF and piercing the periosteum to reach the subperiosteal plane. When performing a subperiosteal injection, the needle must penetrate through periosteum and rest on bone between the periosteum and the bone. From a safety standpoint, when the needle is on bone, it cannot be in a blood vessel, as the subperiosteal plane is an avascular plane. Typically approximately 0.3 cc is injected in this area prior to repositioning needle. Recommended injection protocols for safety include but are not limited to: aspirating prior to injection, and inject the recommended amounts (generally 0.1 cc) at a time.

The method may continue by injecting along TLF up to hairline, typically 2 to 3 cc on each side. The operator then molds the product into a natural, three dimensional shapes with smooth transition into the forehead bone. Continuing further back into the scalp beyond the hairline may help patients that require a more lifting effect. This provides more camouflage and provides significant lifting effect of the mid-face and the corner of the eyes.

The method of reshaping a body part may include the steps of injecting filler into the subperiosteal plane at various locations on the face/head, generally starting at the forehead and going upward/backward from the eyebrow along the temporal line of fusion, and finishing in the mid-face and jaw line, still subperiosteal. Then the method may further include injecting material into sub-dermal areas (not subperiosteal) to provide finishing touches.

Figure 2:
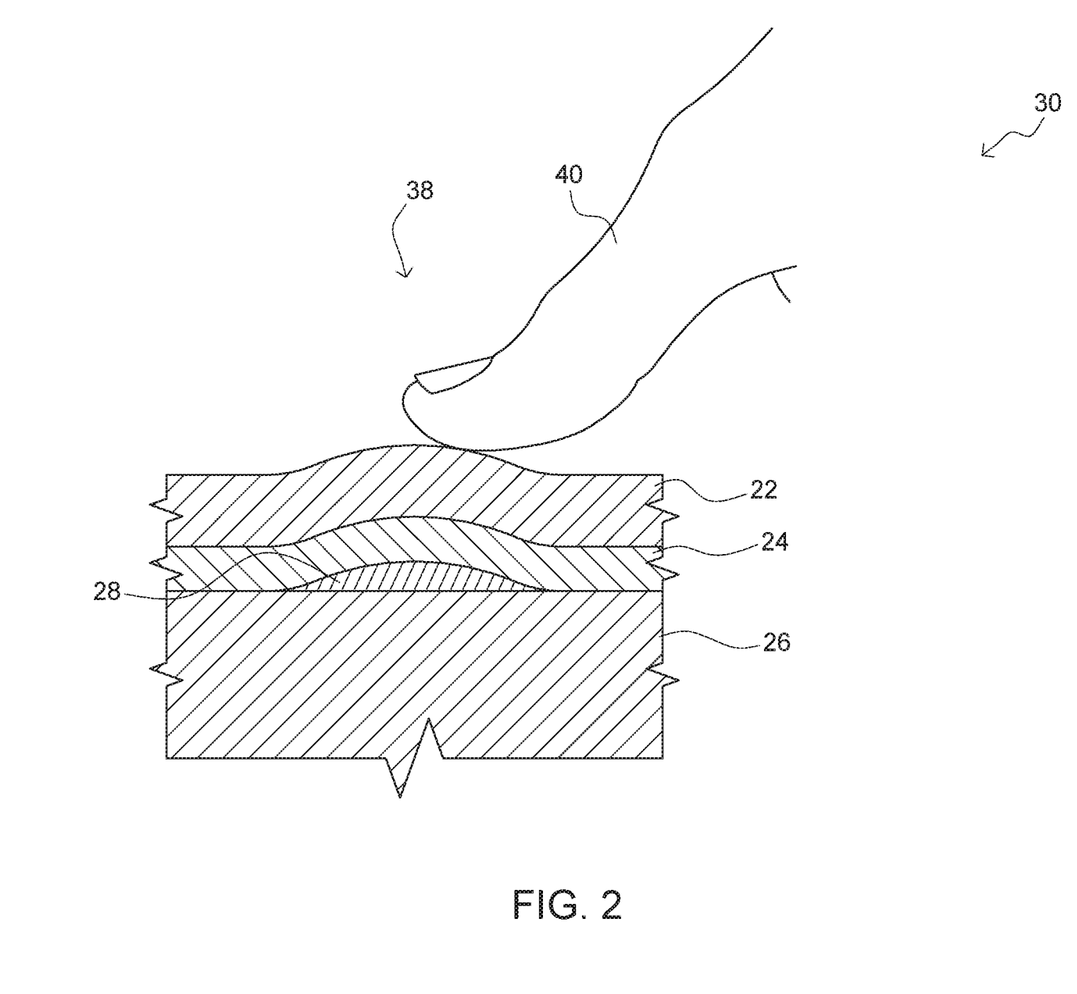
FIG. 2 is a partial side elevational cross-sectional view of a body part having a step of applying pressure to a body of filler of a method of reshaping a body part carried out thereon, according to one embodiment of the invention.

FIG. 2 is a partial side elevational cross-sectional view of a body part having a step of applying pressure 38 to a body of filler 28 of a method of reshaping a body part 30 carried out thereon, according to one embodiment of the invention. There is shown a method of reshaping a body part 30 such as but not limited to a face/skull, specifically the step of applying pressure 38 to the body of filler material 28, such as but not limited to with a finger/thumb 40 to adjust a shape of the body of filler material 28 that is disposed in a subperiosteal plane between a bone 26 and periosteum 24 below the dermis/skin 22 of the body part 30.

The illustrated method of reshaping a face 30 includes the step of applying pressure to the body of filler to adjust a shape of the body of filler 38. The illustrated step 38 includes a finger or a thumb 40 (or other blunt/shaped structure such as but not limited to a shaping mask, form, mold, or the like or combinations thereof) applying pressure through the skin 22 and periosteum 24 against a body of filler 28 deposited on top of a bone 26. The illustrated thumb 40 manipulates the body of filler 28 to a desired shape thereby creating a natural contour to the skin of the face. A facial region wherein filler is deposited/injected may be selected from the group of facial regions consisting of the: forehead, eyebrow, temporal line of fusion, skull, the zygoma, the malar, and the jaw line. The step of injecting is generally repeated in the following order of priority: first the temporal line of fusion, second the zygoma, third the malar, and fourth the jaw line. The method may also include one or more steps of injecting a quantity of material subdermally to a facial region not having a bone backing.

Figure 3:
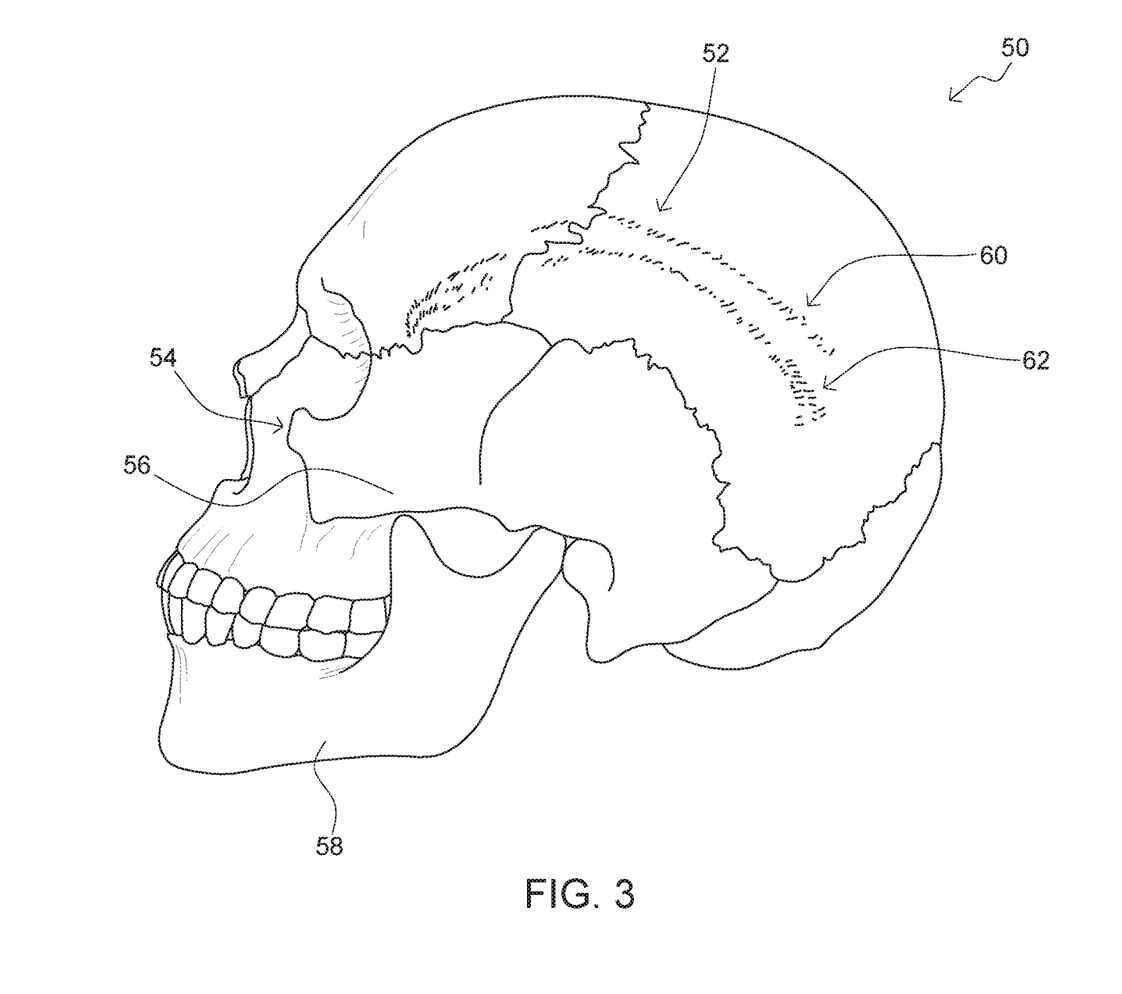
FIG. 3 is a side elevational view of a skull, according to one embodiment of the invention.
Figure 4:
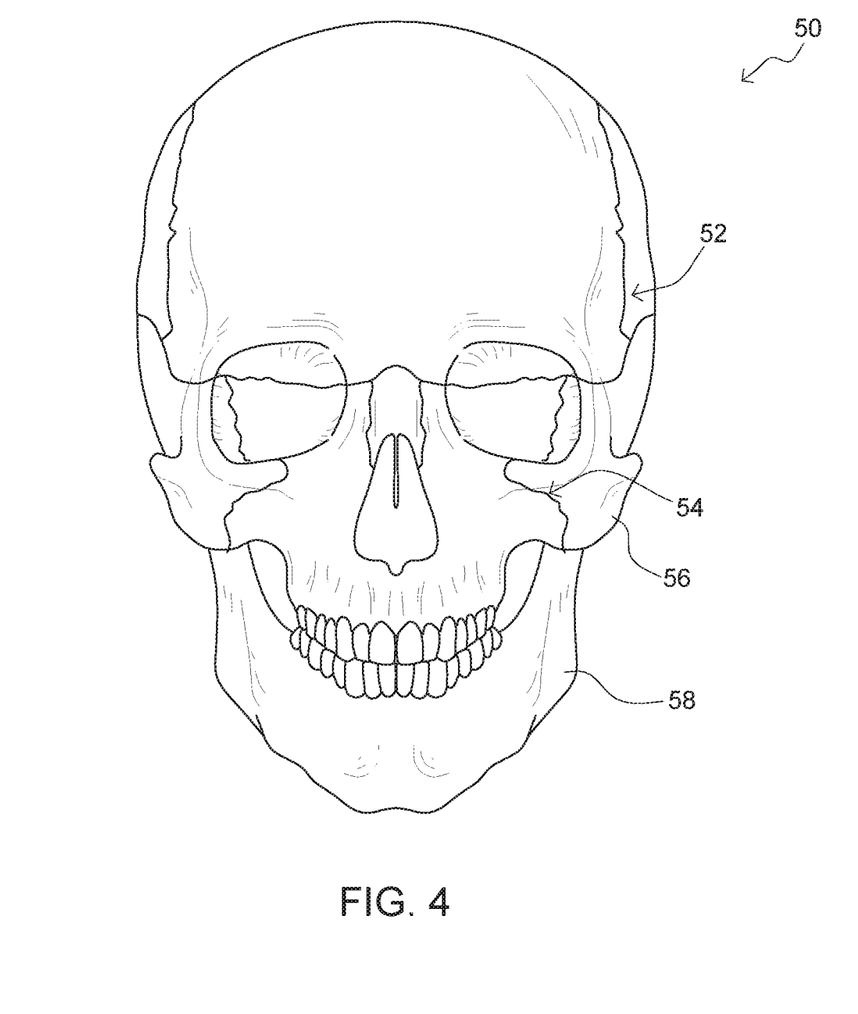
FIG. 4 is a front elevational view of a skull, according to one embodiment of the invention.

FIGS. 3 and 4 illustrate a side elevational view and a front elevational view of a skull, according to one embodiment of the invention. There is shown a skull 50, specifically a temporal line of fusion 52, zygoma 54, malar 56, and jaw line 58.

The temporal line of fusion 52 is where the muscles stop connecting on the sides of the forehead starting at the eyebrows and on up into their hairline. The temporal line of fusion 52 includes a superior region 60 with no significant muscle mass and an inferior region 62 with significant muscle mass.

The skull 50 is a bony structure in the head of most vertebrates (in particular, craniates) that supports the structures of the face and forms a protective cavity for the brain. The skull is composed of two parts: the cranium and the mandible. The skull forms the most anterior portion of the skeleton and is a product of encephalization, housing the brain, many sensory structures (eyes, ears, nasal cavity), and the feeding system. Functions of the skull include protection of the brain, fixing the distance between the eyes to allow stereoscopic vision, and fixing the position of the ears to help the brain use auditory cues to judge direction and distance of sounds. The skull is made of a number of fused flat bones. The skull is part of the skeleton of the head of a vertebrate forming a bony or cartilaginous case that encloses and protects the brain and chief sense organs and supports the jaws.

Crossing the middle of the parietal bone in an arched direction is the temporal line of fusion 52, which includes two curved lines, the superior temporal line of fusion 60 and the inferior temporal line of fusion 62; the former gives attachment to the temporal fascia, and the latter indicates the upper limit of the muscular origin of the temporal muscle.

In the human skull 50, the zygomatic bone or zygoma 54, which is a slender bony process of the zygomatic arch (cheekbone, malar bone) is a paired bone which articulates with the maxilla, the temporal bone, the sphenoid bone and the frontal bone. It is situated at the upper and lateral part of the face and forms the prominence of the cheek, part of the lateral wall and floor of the orbit, and parts of the temporal and infratemporal fossa. It presents a malar 56 and a temporal surface. The malar 56 relates to the cheek or the side of the head. The malar surface 56 is generally convex and perforated near its center by a small aperture, the zygomaticofacial foramen, for the passage of the zygomaticofacial nerve and vessels; below this foramen is a slight elevation, which gives origin to the Zygomaticus.

The temporal surface, directed posteriorly and medially, is concave, presenting medially a rough, triangular area, for articulation with the maxilla (articular surface), and laterally a smooth, concave surface, the upper part of which forms the anterior boundary of the temporal fossa, the lower a part of the infratemporal fossa. Near the center of this surface is the zygomaticotemporal foramen for the transmission of the zygomaticotemporal nerve. The orbital surface forms the lateral part and some of the inferior part of the bony orbit. The zygomatic nerve passes through the zygomatic-orbital foramen on this surface. The lateral palpebral ligament attaches to a small protuberance called the orbital tubercle. The jaw line is the line of the face of the skull formed by the lower jaw, it is the bottom edge of a person's face.

Figure 5:
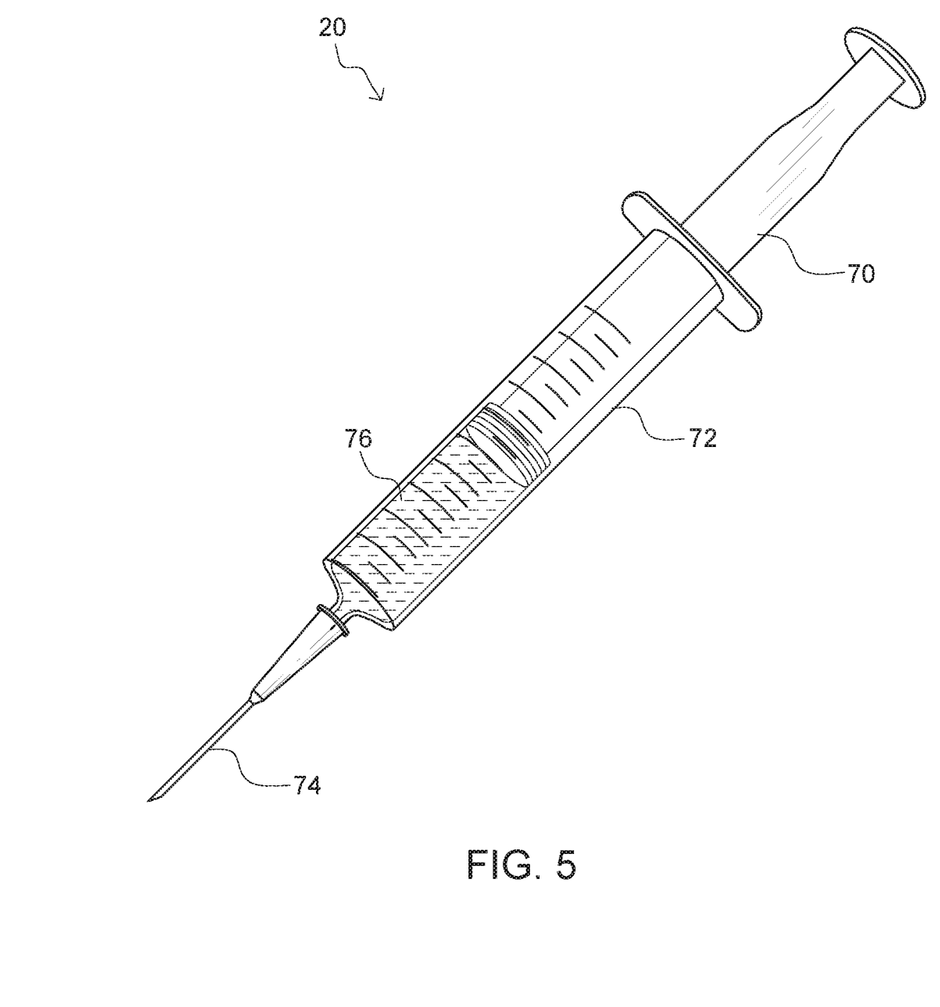
FIG. 5 is a perspective view of a syringe, according to one embodiment of the invention.

FIG. 5 is a perspective view of a syringe, according to one embodiment of the invention. There is shown a syringe 20 including a plunger 70, a tube/chamber 72 having a body of filler material 74 disposed therein, and a hypodermic needle 74 having a needle tip and channel therethrough through which material from the chamber may be communicated out through the needle tip with the plunger is depressed.

According to one embodiment of the invention, there is a syringe 20, which is a simple pump consisting of a plunger 70 that fits tightly in a tube 72. The plunger 70 may be pulled and pushed along the inside the cylindrical tube 72 (called a barrel), allowing the syringe 20 to take in and expel a liquid or gas or a body filler material 76 through an orifice at the open end of the tube. The open end of the syringe is fitted with a hypodermic needle 74, or a nozzle, or tubing to help direct the flow into and out of the barrel. Syringes are often used to administer injections, insert intravenous drugs into the bloodstream, apply compounds such as glue or lubricant, and measure liquids.

According to one embodiment of the invention, there is a method of reshaping a body part. The method includes the step of injecting a quantity of filler material into a subperiosteal plane of the body part thereby depositing a body of filler between a periosteum and bone of the body part with a syringe 20. The method includes the step of piercing a periosteum of the body part with a syringe 20. The method of reshaping a body part includes the step of drawings backwards a plunger 70 of the syringe 20 to ascertain whether a tip of a needle 74 of the syringe 20 is within a blood vessel. The body of filler material 76 includes a hyaluronic acid gel.

Figure 6:
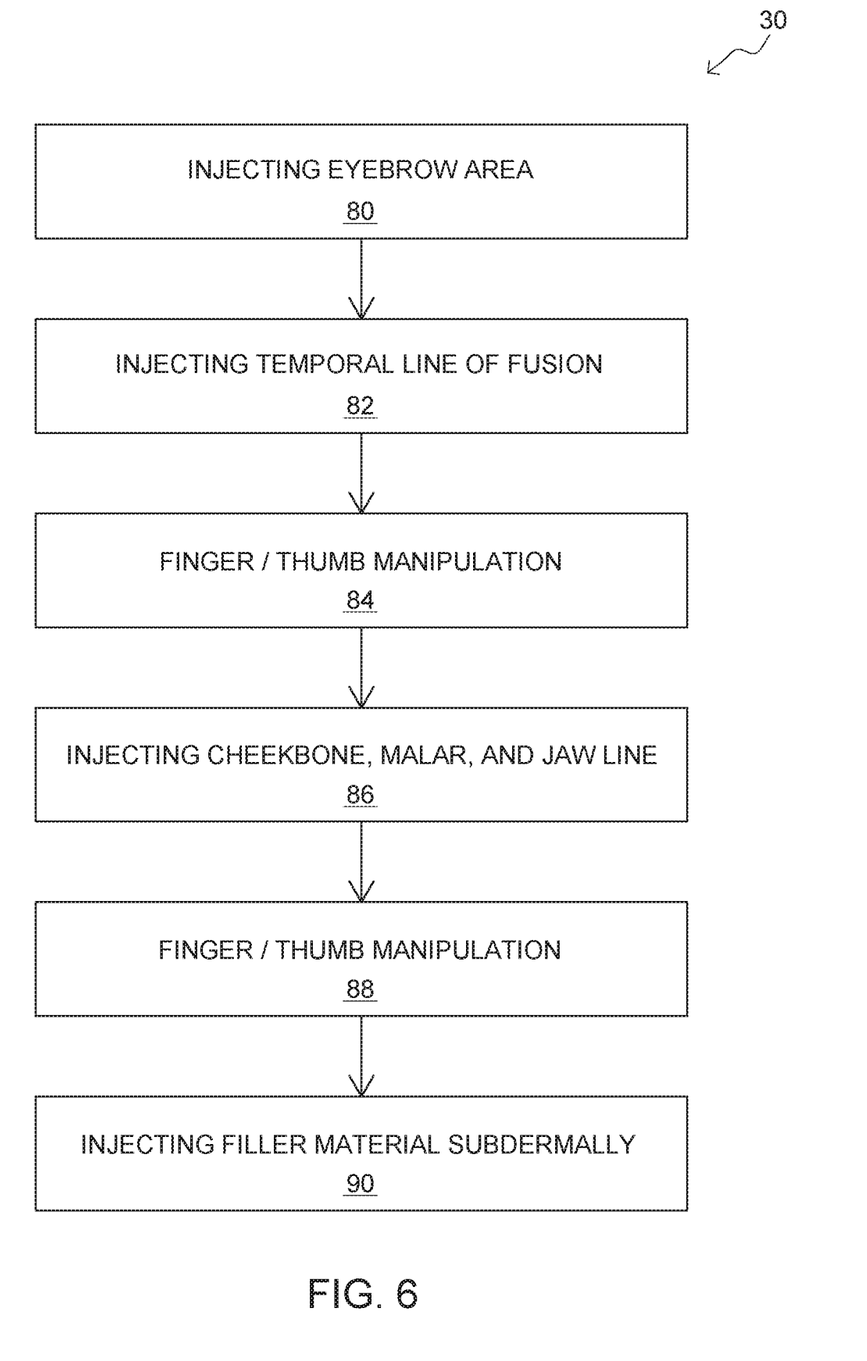
FIG. 6 is a flowchart of a method of reshaping a face, according to one embodiment of the invention.

FIG. 6 is a flowchart of a method of reshaping a face, according to one embodiment of the invention. There is shown a method of reshaping a body part, such as a face 30, specifically the steps of priority when reshaping the face.

The illustrated method of reshaping a face 30 include the step of injecting a quantity of filler material into a subperiosteal plane of a facial region thereby depositing a body of filler between the periosteum and bone of the facial region. The method further includes the step of piercing a periosteum of the facial region with a syringe. The method of reshaping a face includes the step of drawing backwards a plunger of the syringe to ascertain whether a tip of a needle of the syringe is within a blood vessel. The filler may include a hyaluronic acid gel and/or other material appropriate for subperiosteal injection/deposition. The illustrated method of reshaping a face 30 includes the step of injecting an eyebrow area 80, the injecting around the temporal line of fusion 82 followed by finger/thumb manipulation 84, then injecting around the cheekbone, malar and jaw line 86 also followed by finger/thumb manipulation 88, and then injecting filler material subdermally as needed 90. The method of reshaping a face 30 includes the step of injecting the eyebrow area 80 and skipping the injecting the temporal line of fusion and finger/thumb manipulation and going straight to the step of injecting the cheekbone, malar, and the jaw line 86.

The method of reshaping a face 30 includes the step of applying pressure to the body of filler to adjust a shape of the body of filler. A facial region is selected from the group of facial regions consisting of: the temporal line of fusion, the zygoma, the malar, and the jaw line. The step of injecting is repeated in the following order of priority: first the temporal line of fusion, second the zygoma, third the malar, and fourth the jaw line. The method 30 includes injecting areas in combinations, but first the temporal line of fusion, then the zygoma, then the malar, and then the jaw line. Each area may be injected, however, the priority of the areas must remain the same; wherein the temporal line of fusion is injected first, and then secondly the zygome or cheekbone, and then thirdly the malar, and then fourthly the jaw line. The priority of injections must start at the upper most point of the skull and continues injecting downwardly down the skull or face, always injecting the highest point and working downwardly. The method of reshaping a face 30 also includes the step of injecting a quantity of filler material subdermally to a facial region not having a bone backing 90, such as a lip region.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

For example, although the typical recommended injection volume is generally 0.1 cc, it is understood that such may vary according to desired parameters, including but not limited to specific filler materials and/or properties, desired shaping effects, the health of the recipient, the body mass of the recipient, and the like and combinations thereof.

Additionally, although the figures illustrate a particular style of syringe being used to inject filler, there are a plethora of syringes that may be used. Further, as used herein, syringe includes any device which may be used to inject material into the desired location(s), and as such will generally include a channel for conducting filler to the desired location(s) and a chamber for containing material to be injected. Thus a "syringe" may include a more permanent injection fixture such as those used to dispense medicine sub-dermally to patients, such as but not limited to those used with insulin pumps.

It is also envisioned that body parts other than faces may be shaped herewith and that the order of injections may, in such cases, also follow the principle of top-down order of injections or may follow another order based on the stresses/strains placed on the regions of the body part (e.g. elbows/knees may need a concentric application instead of top-down).

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. A method of reshaping a face, comprising the step of injecting a quantity of a filler material into a sub-periosteal plane of the face thereby depositing a body of the filler material between a periosteum and a bone of the face, wherein the step of injecting is at the following locations in the following order: first a temporal line of fusion, second a zygoma, and third a malar.

2. The method of claim 1, further comprising the step of piercing the periosteum of the face with a syringe.

3. The method of claim 1, further comprising the step of drawing backwards a plunger of a syringe to ascertain whether a tip of a needle of the syringe is within a blood vessel.

4. The method of claim 1, wherein the filler material includes a hyaluronic acid gel.

5. The method of claim 1, further comprising the step of applying pressure to the body of the filler material to adjust a shape of the body of the filler material.

6. A method of reshaping a face, comprising Mg step of injecting a quantity of a filler material into a sub-periosteal plane of a facial region thereby depositing a body of the filler material between a periosteum and a bone of the facial region, wherein the step of injecting occurs in at least two of the following locations and is repeated in the following order of priority: first a temporal line of fusion, second a zygoma, and third a malar, and fourth a jaw line.

7. The method of claim 6, further comprising the step of piercing the periosteum of the facial region with a syringe.

8. The method of claim 6, further comprising the step of drawing backwards a plunger of a syringe to ascertain whether a tip of a needle of the syringe is within a blood vessel.

9. The method of claim 6, wherein the filler material includes a hyaluronic acid gel.

10. The method of claim 6, further comprising the step of applying pressure to the body the II filler material to adjust a shape of the body of the filler material.

11. The method of claim 6, wherein the step of injecting includes injection into each of the facial regions consisting of: the temporal line of fusion, the zygoma, the malar, and the jaw line.

12. A method of reshaping a face, comprising the step of injecting a quantity of a filler material into a sub-periosteal plane of a facial region thereby depositing a body of the filler material between a periosteum and a bone of the facial region, wherein the facial region is selected from a group of facial regions consisting of: a temporal line of fusion, zygoma, a malar, and a jaw line and wherein the step of injecting is repeated in the following order of priority: first the temporal line of fusion, second the zygoma, third the malar, and fourth the jaw line.

13. The method of claim 12, further comprising the step of piercing the periosteum of the facial region with a syringe.

14. The method of claim 13, further comprising the step of drawing backwards a plunger of the syringe to ascertain whether a tip of a needle of the syringe is within a blood vessel.

15. The method of claim 14, wherein the filler material includes a hyaluronic acid gel.

16. The method of claim 15, further comprising the step of applying pressure to the body of the filler material to adjust a shape of the body of the filler material.

17. The method of claim 12, further comprising the step of injecting another quantity of filler material subdermally to another facial region not having a bone backing.

* * * * *